United States Patent [19]
Rudnic et al.

[11] Patent Number: 5,430,021
[45] Date of Patent: Jul. 4, 1995

[54] HYDROPHOBIC DRUG DELIVERY SYSTEMS

[75] Inventors: Edward M. Rudnic, No. Potomac, Md.; John A. McCarty, Biscayne Park, Fla.; George W. Belenduik, Potomac, Md.

[73] Assignee: Pharmavene, Inc., Gaithersburg, Md.

[21] Appl. No.: 210,014

[22] Filed: Mar. 18, 1994

[51] Int. Cl.⁶ .................... A61K 9/14; A61K 37/02
[52] U.S. Cl. .................... 514/14; 424/410; 424/457; 424/458; 424/459; 424/461; 424/463; 424/488; 424/490; 424/491; 424/493; 424/498; 424/499; 424/502; 514/15; 514/16; 514/17; 514/18; 514/19
[58] Field of Search .............. 514/14, 15, 16, 17, 514/18, 19; 424/410, 457, 458, 459, 461, 463, 488, 490, 493, 498, 502, 491, 499

[56] References Cited

U.S. PATENT DOCUMENTS

| | | | |
|---|---|---|---|
| 4,629,621 | 12/1986 | Snipes | 424/498 |
| 4,842,863 | 6/1989 | Nishimura et al. | 424/502 |
| 4,861,598 | 8/1989 | Oshlack | 424/468 |
| 4,904,479 | 2/1990 | Illum | 424/502 |
| 4,935,246 | 6/1990 | Ahrens | 424/502 |
| 4,971,804 | 11/1990 | Ghebre-Sellassie et al. | 424/498 |
| 4,994,279 | 2/1991 | Aoki et al. | 424/498 |
| 5,023,089 | 6/1991 | Sakamoto et al. | 424/498 |
| 5,055,304 | 10/1991 | Makino et al. | 424/502 |
| 5,110,606 | 5/1992 | Geyer et al. | 424/502 |
| 5,126,145 | 6/1992 | Evenstad et al. | 424/502 |
| 5,134,122 | 7/1992 | Orsolini | 514/14 |
| 5,185,147 | 2/1993 | Papsidero | 514/14 |
| 5,192,741 | 3/1993 | Orsolini et al. | 514/14 |
| 5,234,695 | 8/1993 | Hobbs et al. | 424/502 |
| 5,270,055 | 12/1993 | Moest | 424/498 |

FOREIGN PATENT DOCUMENTS

| | | |
|---|---|---|
| 257932 | 11/1962 | Australia. |
| 4-8366 | 1/1992 | Japan. |
| 2154874 | 9/1985 | United Kingdom. |

Primary Examiner—Ronald W. Griffin
Attorney, Agent, or Firm—Carella, Byrne, Bain, Gilfillan, Cecchi, Stewart & Olstein

[57] ABSTRACT

A pharmaceutical preparation including a drug incorporated into hydrophobic particles comprised of long chain carboxylic acid or ester thereof or long chain alcohol, wherein the particles are incorporated into a unit dosage form and are individually coated with an enteric coating and/or the unit dosage form includes an enteric protective material.

9 Claims, No Drawings

HYDROPHOBIC DRUG DELIVERY SYSTEMS

The ability of drugs to be administered via the oral route depends on several factors. The drug must be soluble in the gastrointestinal fluids in order for the drug to be transported across biological membranes, or be suitable for an active transport mechanism. Very small particulates (less than 300 nanometers) can be absorbed through the lymphatic system via the Peyer's Patch system in the intestinal tract. However, this mechanism is not capable of absorbing large doses of drugs into the systemic circulation.

A problem arises for hard to dissolve drugs. In the case of conventional drugs, some drugs are relatively insoluble in gastrointestinal fluids. If the extent of solubility is low, this may cause incomplete and/or erratic absorption. If the rate of solubility is low, then absorption will most probably be erratic on an intra-patient and inter-patient basis. Peptide drugs can be water soluble, and these are not as problematic as insoluble peptides. Like conventional drugs, insoluble peptides typically exhibit incomplete or low extent of absorption and erratic absorption or bioavailability.

The primary issue in the ability to deliver peptides orally is the protection of the drug from proteolytic enzymes. There are two basic approaches to do this. The first is an "enteric" coating that can be applied to release the drug only in neutral to basic Ph (usually Ph 6-8), so that the peptide is not exposed to gastric juices. However, this approach alone is not sufficient to protect the peptide since proteolytic enzymes exist in the upper intestinal tract, and some degradation of the drug can still occur. The other approach is to incorporate the peptide in a hydrophobic material so that aqueous fluids cannot penetrate the system. It is important to select a hydrophobic material that can erode or slowly dissolve in the intestinal tract so that the drug is released. In this way, the peptide is protected from proteolytic enzymes. In addition, it is possible to combine the two approaches.

However, there are inherent difficulties with the approach outlined above. First, many drugs are released too slowly from hydrophobic systems. Also, some peptides will partition into the hydrophobic phase so that they will not be fully released from these systems. Thus, both the rate and extent of drug release are crucial components of any drug delivery system, and are even more important for many peptide drugs.

The present invention provides a pharmaceutical composition wherein the pharmaceutical agent or drug (which may be a therapeutic, diagnostic or prophylactic agent) is incorporated into finely divided hydrophobic particles which are formed from a hydrophobic material selected from the group consisting of a long chain carboxylic acid, a long chain carboxylic acid ester, a long chain carboxylic acid alcohol and mixtures thereof. The particles preferably are coated with a sustained release and/or enteric coating and incorporated into an appropriate oral delivery dosage form or in the alternative are incorporated into a dosage form which includes a sustained release and/or enteric coating.

In accordance with the present invention certain hydrophobic carrier systems provide enhanced absorption capabilities for oral delivery of peptide drugs and drugs that are poorly soluble in aqueous media. The hydrophobic materials in the carrier system are selected from the group consisting of long chain carboxylic acids, long chain carboxylic acid esters, long chain carboxylic acid alcohols and mixtures thereof.

The long chain carboxylic acids, generally contain from 6–30 carbon atoms and preferably contains at least 12 carbon atoms, most preferably 12 to 22. In some cases this carbon chain is fully saturated and unbranched, while others contain one or more double bonds. A few contain 3-carbon rings or hydroxyl groups. Examples of saturated straight chain acids are n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid and melissic acid. Also uselful are unsaturated monoolefinic straight chain monocarboxylic acids. Examples of these are oleic acid, gadoleic acid and erucic acid. Also useful are unsaturated (polyolefinic) straight chain monocaboxyic acids. Examples of these are linoleic acid, linolenic acid, arachidonic acid and behenolic acid. Useful branched acids include, for example, diacetyl tartaric acid.

Examples of long chain carboxylic acid esters include, but are not limited to, those from the group of: glyceryl monostearates; glyceryl monopalmitates; mixtures of glyceryl monostearate and glyceryl monopalmitate (Myvaplex 600, Eastman Fine Chemical Company); glyceryl monolinoleate; glyceryl monooleate; mixtures of glyceryl monopalmitate, glyceryl monostearate, glyceryl monooleate and glyceryl monolinoleate (Myverol 18–92, Eastman Fine Chemical Company); glyceryl monolinolenate; glyceryl monogadoleate; mixtures of glyceryl monopalmitate, glyceryl monostearate, glyceryl monooleate, glyceryl monolinoleate, glyceryl monolinolenate and glyceryl monogadoleate (Myverol 18–99, Eastman Fine Chemical Company); acetylated glycerides such as distilled acetylated monoglycerides (Myvacet 5-07, 7-07 and 9–45, Eastman Fine Chemical Company); mixtures of propylene glycol monoesters, distilled monoglycerides, sodium stearoyl lactylate and silicon dioxide (Myvatex TL, Eastman Fine Chemical Company); mixtures of propylene glycol monoesters, distilled monoglycerides, sodium stearoyl lactylate and silicon dioxide (Myvatex TL, Eastman Fine Chemical Company) d-alpha tocopherol polyethylene glycol 1000 succinate (Vitamin E TPGS, Eastman Chemical Company); mixtures of mono- and di-glyceride esters such as Atmul-84 (Humko Chemical Division of Witco Chemical); calcium stearoyl lactylate; ethoxylated mono- and di-glycerides; lactated mono- and diglycerides; lactylate carboxylic acid ester of glycerol and propylene glycol; lactylic esters of long chain carboxylic acids; polyglycerol esters of long chain carboyxlic acids, propylene glycol mono- and di-esters of long chain carboxylic acids; sodium stearoyl lactylate; sorbitan monostearate; sorbitan monooleate; other sorbitan esters of long chain carboxylic acids; succinylated monoglycerides; stearyl monoglyceryl citrate; stearyl heptanoate; cetyl esters of waxes; stearyl octanoate; $C_{10}$–$C_{30}$ cholesterol/lavosterol esters; and sucrose long chain carboxylic acid esters.

The alcohols useful in the invention are exemplified by the hydroxyl forms of the carboxylic acids exemplified above and also cetearyl alcohol.

The types of protective or sustained release coatings that can be used include, but are not limited to, ethylcellulose, hydroxypropylmethylcellulose, hydroxypropylcellulose, hydroxyethylcellulose and esters of methacrylic and ethacrylic acid (Eudragit RL, RS, and NE polymer products, Rohm Pharma, Darmstadt, Ger-many). The enteric protective materials or coatings can be, for example, cellulose acetate pthalate, hydroxypropylmethylcellulose pthalate, ethylvinylacetate pthalate, polyvinylacetate pthalate and esters of methacrylic and ethacrylic acid (Eudragit S and Eudragit L, Rohm Pharma, Darmstadt, Ger.).

The drugs to be incorporated individually or as combinations in the pharmaceutical preparations of the invention are those having less than about 80% oral bioavailability. The term "bioavailability" as used here means the rate and extent of systemic absorption of a drug from the oral route of administration.

In one aspect, the drug is a polypeptide, usually of less than about 15 amino acids. Examples include cyclosporin, angiotensin I, II and III, enkephalins and their analogs, ACTH, antiinflammatory peptides I, II, III, bradykinin, calcitonin, cholecystikinin (CCK) fragments 26–33 and 30–33, pre/pro CCK (V-9-M), β-endorphin, dinorphin, leucokinin, leutinizing hormone releasing hormon (LHRH), neurokinins (e.g. neurokinin A), somatostatin, substance P, thyroid releasing hormone (TRH) and vasopressin.

In another aspect, the drug is an organic molecule that is poorly soluble in aqueous media. These organic molecules usually have a molecular weight (m.w.) of less than about 1,000 daltons, and usually less than about 600 daltons. Examples include acyclovir, adriamycin, cabamazepine, griseofulvin, angiotensin converting enzyme inhibitors, flutamide, melphalan, nifedipine, indomethacin, naproxen, estrogens, testosterones, steroids, phenytoin, sumatriptan, ergotamines and cannabinoids.

In accordance with the invention, drugs are incorporated into hydrophobic materials by admixture using conventional mixing devices and homogenizers used for semi-solid ointments and lotions, with agitation at speeds common to emulsified products such as creams and emulsions. Examples of common equipment employed are propeller or turbine mixers, homogenizers, colloid mills, ultrasonic mixers and microfluidizers. The shear of the agitation should be sufficient to form a stable dispersion, but not too great to cause degradation of the drug. Suitable homogenizers are available from Micromedics, Inc., Silverson, APV Crepaco, and Arde Barinco.

Using these devices, the mixture of drug in the hydrophobic material is formed into particles, e.g. beads or spheres, by spray-congealing or "prilling". This process uses a spray nozzle which atomizes the material in a cooling tower or chamber. As the material is sprayed, surface tension causes a uniform spherical bead to be formed. As the bead falls through the cooling chamber, it hardens into a stable, intact sphere.

The particles generally have a particle size of from 0.5 microns to 100 microns. It is preferred to reduce the size of the sphere as much as possible, most preferably below 10 microns. Optionally, the particles are coated with a sustained-release coating and/or an enteric coating to modify the rate of drug release from the particles.

The particles can be incorporated into hard gelatin capsules, either with additional excipients, or alone. Typical excipients to be added to a capsule formulation include, but are not limited to: fillers such as microcrystalline cellulose, soy polysaccharides, calcium phosphate dihydrate, calcium sulfate, lactose, sucrose, sorbitol, or any other inert filler. In addition, there can be flow aids such as fumed silicon dioxide, silica gel, magnesium stearate, calcium stearate or any other material imparting flow to powders. Because of their hydrophobic nature, the particles should not need a lubricant, but one can be added if necessary by using polyethylene glycol, leucine, glyceryl behenate, magnesium stearate or calcium stearate.

The particles may also be incorporated into a tablet, in particular by incorporation into a tablet matrix, which rapidly disperses the particles after ingestion. In order to incorporate these particles into such a tablet, a filler/binder must be added to a tablet that can accept the particles, but will not allow their destruction during the tableting process. Materials that are suitable for this purpose include, but are not limited to, microcrystalline cellulose (Avicel), soy polysaccharide (Emcosoy), pre-gelatinized starches (STARCH 1500, National 1551), and polyethylene glycols (Carbowax). The materials should be present in the range of 5–75% (w/w), with a preferred range of 25–50% (w/w).

In addition, disintegrants are added in order to disperse the particles once the tablet is ingested. Suitable disintegrants include, but are not limited to: cross-linked sodium carboxymethyl cellulose (Ac-Di-Sol), sodium starch glycolate (Explotab, Primojel), and cross-linked polyvinylpolypyrrolidone (Plasdone-XL). These materials should be present in the range of 3–15% (w/w), with a preferred range of 5–10 (w/w).

Lubricants are also added to assure proper tableting, and these can include, but are not limited to: magnesium stearate, calcium stearate, stearic acid, polyethylene glycol, leucine, glyceryl behanate, and hydrogenated vegetable oil. These lubricants should be present in amounts from 0.1–10% (w/w), with a preferred range of 0.3–3.0% (w/w).

Tablets are formed, for example, as follows: the particles are introduced into a blender along with Avicel, disintegrants and lubricant, mixed for a set number of minutes to provide a homogeneous blend which is then put in the hopper of a tablet press with which tablets are compressed. The compression force used is adequate to form a tablet; however, not sufficient to fracture the beads or coatings.

The tablet or capsule can also be enteric coated. Either the particles can be enteric coated (Ph sensitive) and released in the stomach or the capsule or tablet can be enteric coated (thereby releasing the particles in the intestine), in which case the particles need not be so coated. To use only a sustained release coating on the particle one would also need an enteric coated capsule. There are three approaches here. First, there is the uncoated hydrophobic particle in an enteric coated capsule. Second, there is the sustained release coated particle within an enteric coated capsule. Third, there is the enteric coated particle enclosed within a regular soft gelatin capsule.

EXAMPLE 1

This example illustrates the preparation of uncoated particles according to the invention for delivery of calcitonin.

| Ingredients | % W/W |
| --- | --- |
| Calcitonin | 10 |
| Glyceryl Monostearate | 20 |
| Glyceryl Ricinoleate | 5 |
| Microcrystalline Cellulose | 60 |
| Silicon Dioxide | 5 |

The particles are prepared as follows. The glyceryl monostearate and glyceryl ricinoleate are melted at 60° C. and calcitonin is added to the resultant liquid. Microcrystalline cellulose and silicon dioxide are blended into the mixture while it is cooled to 40° C. This mixture is prilled (spray congealed) into particles. These uncoated particles are suitable to be enclosed within an enteric, and optionally sustained release, coated tablet or capsule.

EXAMPLE 2

This example illustrates the preparation of particles with a sustained release coating, hydroxypropylmethylcellulose, according to the invention for delivery of cyclosporin.

| Ingredients | % W/W |
| --- | --- |
| Cyclosporin | 5 |
| Glyceryl Monoglycerate | 30 |
| Vitamin E TPGS | 20 |
| Hydroxypropylmethylcellulose (HPMC) | 5 |
| Water | 40 |

The particles are prepared as follows. The cyclosporin is dissolved in melted glyceryl monostearate and Vitamin E TPGS at 60° C. The HPMC(sustained release coating) is dispersed and dissolved in hot water and this is cooled to 20°-25° C. The hydrophobic phase is added to the hydrophilic phase slowly, while mixing rapidly, until both phases are dispersed. The mixture is spray-dried into prills/particles while evaporating the water from the mixture. These particles are suitable to be enclosed within an enteric coated tablet or capsule.

EXAMPLE 3

This example illustrates the preparation of particles coated with an enteric coating, hydroxypropylmethyl cellulose phthalate, in accordance with the invention for delivery of somatostatin.

| Ingredients | % W/W |
| --- | --- |
| Somatostatin | 10 |
| Calcium Stearoyl Lactylate | 15 |
| Glyceryl Monooleate | 25 |
| Starch 1551 | 20 |
| Microcrystalline Cellulose | 25 |
| Triethyl Citrate | 0.25 |
| Hydroxypropylmethylcellulose (HPMC) | 2 |
| Hydroxyproplymethlycellulose Pthalate (HPMC Pthalate) | 3 |

The particles are prepared as follows: The calcium stearoyl lactylate and glyceryl monooleate are melted at 60° C. and Starch 1551 and microcrystalline cellulose are blended in. Ethanol is added to the mixture, which is then cooled rapidly to 30° C. This mixture is prilled, removing ethanol from the particles. The dried particles are coated with an aqueous coating solution made from the HPMC, HPMC Pthalate(enteric coating) and triethyl citrate. These particles are suitable to be put into an uncoated tablet or regular soft gelatin capsule, or a sustained release coated tablet or capsule.

What is claimed is:

1. A pharmaceutical preparation comprising a pharmaceutical agent selected from the group consisting of polypeptides and organic molecules that are poorly soluble in aqueous media incorporated into particles having a diameter of about 0.5 to 100 microns of a hydrophobic carrier comprising at least one hydrophobic material selected from the group consisting of long chain carboxylic acid esters and mixtures thereof in a dose form suitable for oral administration.

2. The pharmaceutical preparation of claim 1 wherein the long chain carboxylic acid ester is selected from the group consisting of glyceryl monostearates; glyceryl monopalmitates; mixtures of glyceryl monostearate and glyceryl monopalmitate; glyceryl monolinoleate; glyceryl monooleate; mixtures of glyceryl monopalmitate, glyceryl monostearate, glyceryl monooleate and glyceryl monolinoleate; glyceryl monolinolenate; glyceryl monogadoleate; mixtures of glyceryl monopalmitate, glyceryl monostearate, glyceryl monooleate; glyceryl monolinoleate, glyceryl monolinolenate and glyceryl monogadoleate; acetylate monoglycerides; mixtures of propylene glycol monoesters, distilled monoglycerides, sodium stearoyl lactylate and silicon dioxide; mixtures of propylene monoesters, distilled monoglycerides, sodium stearoyl lactylate and silicon dioxide; d-alpha tocopherol polyethylene glycol 1000 succinate; mixtures of mono- and di-glyceride esters; calcium stearoyl lactylate; ethoxylated mono- and di-glycerides; lactated mono- and diglycerides; lactylate carboxylic acid esters of glycerol and propylene glycol; lactylic esters of long chain carboxylic acids; polyglycerol esters of long chain carboxylic acids; propylene glycol mono- and di-esters of long chain carboxylic acids; sodium steroyl lactylate; sorbitan monostearate; sorbitan monooleate; other sorbitan esters of long chain carboxylic acids; succinylated monoglycerides; stearyl monoglyceryl citrate; stearyl heptanoate; cetyl esters of waxes; stearyl octanoate; $C_{10}$–$C_{30}$ cholesterol/lavosterol esters; and sucrose long chain carboxylic acid esters.

3. The pharmaceutical preparation of claim 1 wherein the drug is a polypeptide that is poorly soluble in aqueous media and has up to about 15 amino acids.

4. The pharmaceutical preparation of claim 3 wherein the drug is a polypeptide of up to about 12 amino acids.

5. The pharmaceutical preparation of claim 1 wherein the drug is an organic molecule that is poorly soluble in aqueous media and has a m.w. of less than about 1,000 daltons.

6. The pharmaceutical preparation of claim 5 wherein the drug is an organic molecule that has a m.w. of less than about 600 daltons.

7. The pharmaceutical preparation of claim 1 wherein the drug is selected from the group consisting of cyclosporin, angiotensin I, II and III, enkephalins and their analogs, ACTH, antiinflammatory peptides I, II, III, bradykinin, calcitonin, cholecystokinin fragments 26–33 and 30–33, pre/pro cholecystokinin (V-9-M), β-endorphin, dinophin, leucokinin, leutinizing hormone releasing hormone, neurokinins, somatostatin, substance P, thyroid releasing hormone, vasopressin, cabamazepine, griseofulvin, angiotensin converting enzyme inhibitors, flutamide, nifedipine, indomethacin, naproxen, estrogens, testosterones, steroids, phenytoin, ergotamines and cannabinoids.

8. The pharmaceutical preparation of claim 1 wherein the particles are coated with a sustained release coating and encapsulated in a capsule comprising an enteric coating material.

9. The pharmaceutical preparation of claim 1 wherein the particles are coated with an enteric coating and encapsulated in a capsule that is soluble in an acidic aqueous environment.

* * * * *